United States Patent
Choi et al.

(10) Patent No.: US 6,589,765 B1
(45) Date of Patent: Jul. 8, 2003

(54) MASS PRODUCTION OF PACLITAXEL BY CHANGING THE TEMPERATURE OF THE MEDIUM DURING THE PLANT CELL CULTURE

(75) Inventors: Ho-Joon Choi, Daejon (KR); Hyung-Kyoon Choi, Daejon (KR); Sang-Ic Kim, Daejon (KR); Jeong-Hwan Yun, Daejon (KR); Joo-Sun Son, Daejon (KR); Moon-Seok Chang, Daejon (KR); Eunsoo Choi, Daejon (KR); Hong-Rak Kim, Daejon (KR); Seung-Suh Hong, Daejon (KR); Hyun-Soo Lee, Daejon (KR)

(73) Assignee: Samyang Genex Corporation, Seoul (KR)

( * ) Notice: Subject to any disclaimer, the term of this patent is extended or adjusted under 35 U.S.C. 154(b) by 0 days.

(21) Appl. No.: 09/269,154
(22) PCT Filed: Jun. 25, 1998
(86) PCT No.: PCT/KR98/00179
§ 371 (c)(1), (2), (4) Date: Feb. 26, 1999
(87) PCT Pub. No.: WO99/00513
PCT Pub. Date: Jan. 7, 1999

(30) Foreign Application Priority Data

Jun. 26, 1997 (KR) .......................................... 1997-27746
Mar. 12, 1998 (KR) ........................................... 1998-9384

(51) Int. Cl.⁷ ............................................... C12P 17/02
(52) U.S. Cl. ....................... 435/123; 435/127; 435/417; 435/410; 549/510; 549/511
(58) Field of Search ................................ 435/123, 127, 435/417, 410; 549/510, 511

(56) References Cited

U.S. PATENT DOCUMENTS

| | | | |
|---|---|---|---|
| 5,019,504 A | | 5/1991 | Christen et al. |
| 5,407,816 A | * | 4/1995 | Bringi .......................... 435/123 |
| 5,968,789 A | * | 10/1999 | Yukimune .................... 435/123 |

FOREIGN PATENT DOCUMENTS

| | | |
|---|---|---|
| WO | WO 93/17121 | 9/1993 |
| WO | WO 97/21696 | 6/1997 |

* cited by examiner

Primary Examiner—Irene Marx
(74) Attorney, Agent, or Firm—Darby & Darby

(57) ABSTRACT

The present invention relate to a method to increase the production level of paclitaxel by changing the temperature during the plant cell culture. According to the present invention, the production of the paclitaxel comprises the following procedure: (i) cultivating the Taxus genus plant cells in a medium at ca. 20 to 25° C.; and (ii) when growth of the plant cells has progressed sufficiently, changing the cultivation temperature to ca. 26 to 32° C. to continue the culture. The present invention comprises also the method of increasing the paclitaxel production by inoculating the cells at a high initial concentration and by increasing the saccharide concentration in the medium: According to the present invention, paclitaxel can be mass-produced conveniently and therefore has an industrial application.

7 Claims, 3 Drawing Sheets

US 6,589,765 B1

MASS PRODUCTION OF PACLITAXEL BY CHANGING THE TEMPERATURE OF THE MEDIUM DURING THE PLANT CELL CULTURE

This application was filed under 35 U.S.C. 371 as the national phase of PCT/KR 98/00179 filed Jun. 25, 1998.

BACKGROUND OF THE INVENTION

1. Field of the Invention

The present invention relates to a method for mass production of paclitaxel, a secondary metabolite by plant cell culture.

2. Description of the Prior Art

Paclitaxel is one of taxane compounds which are isolated from the bark of *Taxus brevifolia*, and it is effective for the treatment of cancer, such as leukemia. It is reported that paclitaxel is capable of curing approximately 30%, 50% and 20% of ovarian, breast and lung cancers, respectively, by inhibiting depolymerization of microtubules. Generally, paclitaxel can be produced by a total chemical synthesis, by a semi-synthesis employing precursors such as baccatin, direct extraction of paclitaxel from Taxus genus plants or by culturing cells that produce paclitaxel. Among these methods, plant cell culture-based process for paclitaxel production has the following advantages. First, paclitaxel can be produced in a continuous manner regardless of a fluctuation in the supply of yew plants due to damages by blight, and harmful insects or by natural disasters. Secondly, cell cultures can be propagated in large bioreactors, from which paclitaxel can be massively produced by manipulating culture conditions. Thirdly, cell cultures produce a simpler spectrum of compounds compared to other methods, considerably simplifying separation and purification. Fourthly, a cell culture process can adapt quickly to rapid changes in demand better than the other methods. And fifthly, a cell culture process can produce paclitaxel as well as taxane precursors such as baccatin that can be converted to paclitaxel.

Methods for producing paclitaxel by utilizing plant cell culture have been described in the art:

U.S. Pat. No. 5,019,504 discloses a method for producing paclitaxel and its derivatives utilizing cultured cells of Taxus brevifolia. The yield of paclitaxel described therein, however, is 1~3 mg/L with the doubling time for the biomass is 7~12 days which is insufficient for industrial application. Moreover, the production of paclitaxel by the plant culture is unstable and even when a primary cell having high production level is obtained by selection, it is difficult to keep its content by subculturing (E. R. M. Wickremesine et. al., World Congress on Cell and Tissue Culture (1992)).

WO 93/17121 offers a method for paclitaxel production by cell culture of Taxus genus plant while changing composition of the medium, growth rate, and production rate, etc. In case of *Taxus chinensis*, 24.1 mg/L of paclitaxel can be obtained in 18 days of culture and biomass doubles every 2.5 days.

All of these patents describe methods for mass production of paclitaxel by controlling the cell cultivation temperature to 25° C.; there are no teaching in said patents, nor do they anticipate that the changes in the growth rate or production rate when the cell cultivation temperature is varied.

SUMMARY OF THE INVENTION

The object of the present invention is to provide a convenient and efficient method for mass production of paclitaxel.

Another object of the present invention is to provide a convenient method for the production of paclitaxel with high yield by regulating the temperature during the plant cell culture.

Another object of the present invention is to provide a more productive method of producing paclitaxel by inoculating a strain that produces paclitaxel at a high concentration.

BRIEF DESCRIPTION OF THE DRAWINGS

The above and other objects and features of the present invention will become apparent from the following descriptions given in conjunction with the accompanying drawings, in which.

DETAILED DESCRIPTION OF THE INVENTION

Figure 1:
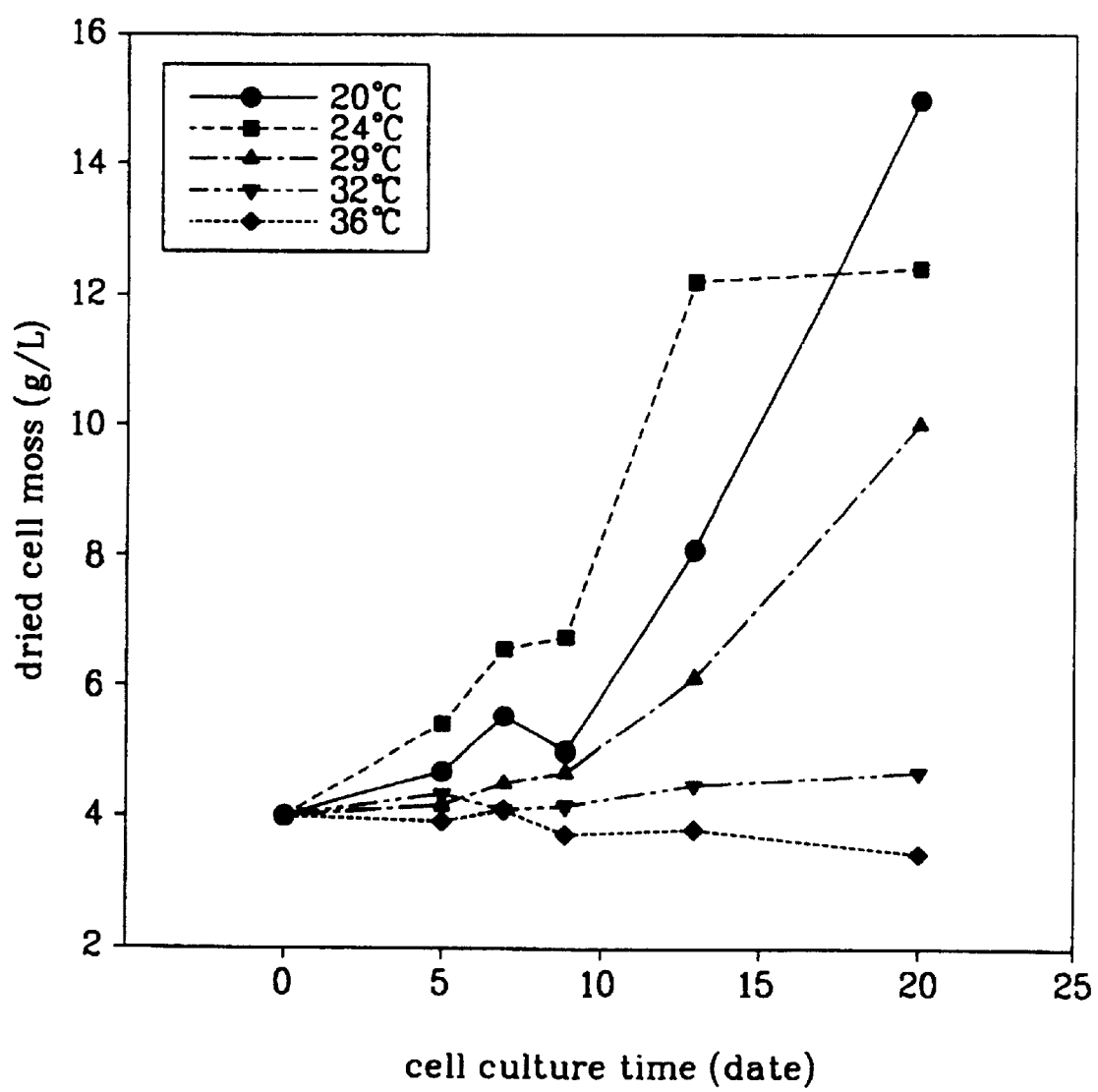
FIG. 1 is a graph showing the effect of temperature in the growth rate of a paclitaxel producing cell line, *Taxus chinensis* SYG-1.

The present invention relates to a method to increase the production level of paclitaxel by changing the temperature during the plant cell culture. More particularly, the present invention comprises a mass production method for obtaining paclitaxel with a high yield by changing the temperature of the culture media for incubation after the growth of the Taxus genus plant cells are sufficiently progressed.

In general, the production of a secondary metabolite from a plant is not related to its growth. Some of the secondary metabolites participate in the protection of the plant from environmental stress. In case of the plant cell culture, one can improve the production of the secondary metabolite by regulating the metabolism that is related to the defense mechanism of the plant. In the present invention, a method to maximize the production level of paclitaxel by changing the temperature during the plant cell culture is developed. Also in the present invention, a method of increasing the production of paclitaxel is developed by increasing the initial number of cells for inoculation and by adjusting the concentration of saccharide in the cell culture medium based on the knowledge that the initial number of cells for the inoculation and the initial concentration of saccharide can affect the metabolism.

The inventors first optimized the temperature for the cell growth, and then tried to find the cultivation temperature in order to increase the production level of paclitaxel by retarding the cells growth. To this end, the inventors have cultivated the Taxus genus plant cells at the optimum growth temperature until sufficient cells were obtained and subsequently grew the cells at a changed temperature to increase the production level of the secondary metabolites including paclitaxel.

According to the present invention, the production of the paclitaxel comprises of the steps of:

(i) cultivating the Taxus genus plant cells in a medium at about 20 to 25° C., preferably at about 20 to 24° C.; and, (ii) when the growth of the plant cells has progressed sufficiently, changing the cultivation temperature to about 26 to 32° C., preferably to about 28 to 30° C. and continuing the cultivation to produce paclitaxel The time-point for the sufficient cell growth can vary depending on the kind of plant cell, the cultivation temperature, the composition of the medium or other conditions. According to the Examples of the present invention, the cell cultivation temperature can be changed 10 days, preferably 14 days or more preferably 21 days after the initiation of the culture.

According to the methods of the present invention, paclitaxel production is increased when cultivation temperature is increased after the cell growth were progressed sufficiently at a slightly low temperature. After inoculating the cells, it is desirable to change the temperature to 26 to 32° C. which is higher than the growth temperature, preferably to 28 to 30° C. It is considered that the changed temperature could be optimum for the production or the activity of the enzymes that participate in the biosynthesis of paclitaxel.

The methods in the present invention is applied to any plants of Taxus genus without any particular limitations. For instance, the method of the present invention can be applied to *Taxus brevifolia, Taxus canadensis, Taxus cuspidata, Taxus baccata, Taxus globosa, Taxus floridana, Taxus wallichiana, Taxus x media* and *Taxus chinensis*.

The medium for the plant cell culture in the present invention is B5 medium supplemented with casein hydrolysate (Gamborg et. al., Exp. Cell Res. 50: 151–158 (1968)). To increase the paclitaxel production level, it is preferable to use the modified B5 medium as shown in Table 1. Moreover, a saccharide, preferably maltose can be added to the medium at day 5 to day 30, at least once and preferably twice; once at day 7 to 12 and another at day 18 to day 24 after the initiation of the culture at a concentration of 10 to 100 g/L, preferably of 10 to 40 g/L for a single dose.

TABLE 1

Taxus genus plant cell culture medium

| composition | concentration (mg/L) |
|---|---|
| *inorganic salts* | |
| $CaCl_2$ anhydride | 113.23 |
| $CoCl_2.6H2O$ | 0.025 |
| $CuSO_4.5H_2O$ | 0.025 |
| $FeSO_4.7H_2O$ | 27.8 |
| $H_3BO_3$ | 3.0 |
| KI | 0.75 |
| $KNO_3$ | 2,500 |
| $MgSO_4.7H_2O$ | 246 |
| $MnSO_4.H_2O$ | 10 |
| $NaH_2PO_4.H_2O$ | 150 |
| $Na_2MoO_4.2H_2O$ | 0.25 |
| $(NH_4)_2SO_4$ | 134 |
| $ZnSO_4.7H_2O$ | 2 |
| *vitamins* | |
| inositol | 10 |
| nicotinic acid | 1 |
| calcium pentosenate | 0.874 |
| pyridoxin.HCl | 1 |
| riboflavin | 0.015 |
| thyamine.HCl | 10 |
| *hormones* | |
| naphthalene acetate | 10 $\mu$M |
| benzylaminopurin | 0.2 $\mu$M |
| casein hydrolysis product | 500 |
| $AgNO_3$ | 1–15 $\mu$M |
| sucrose | 30,000 |

Another method in the present invention comprises the step of inocultating the cells at a higher concentration than normal, for instance at 4 g/L of the dried cell mass. In case the inoculating cells at a higher concentration, it is desirable that the saccharide concentration in medium to be higher than in normal culture, for instance, 40 g/L.

The present invention is further illustrated in the following examples, which should not be taken to limit the scope of the invention.

EXAMPLE 1

Effect of the Cultivation Temperature on the Growth of the Taxus Genus Cells and Paclitaxel Production.

*Taxus chinensis* Hu-1, *Taxus chinensis* SYG-1 (KCTC-0232BP), *Taxus baccata, Taxus x media* and *Taxus cuspidata* cultures were cultivated for 15 days in B5 medium supplemented with 500 mg/L of casein hydrolysate. Each cell culture was inoculated to 75 ml of the medium in Table 1 in a 250 ml Erlenmeyer flask and cultivated for 20 days at 24° C. At day 21, the cultivation temperature was changed to 29° C. The dried cell mass and the amount of produced paclitaxel at days 21 and 42 were measured, and the results are showed in Table 3.

The Dried Cell Mass was Measured by the Following Method.

First, a 5.5 cm filter paper (No. 541, Whatman Co. U.S.A.) was put on a porous funnel equipped with a suction flask. The filter paper was attached on the funnel fully by squirting distilled water thereto. Then, 5 ml of the plant cell culture medium to be analyzed was spread on the filter paper and filtered under reduced pressure to remove the water. The filter paper after the suction was put on a dish made with aluminum foil and dried in an oven at 80° C. for 24 hours. After this procedure, the filter paper was taken out of the oven and left at room temperatures for 10 min before measuring the total weight of the aluminum foil-dish and the filter paper. By subtracting this value from the predetermined weight of the aluminum foil-dish and the filter paper and subsequently by multiplying 200 to the result to obtain the dried cell mass per one liter of the culture medium.

The amount of paclitaxel produced was quantitatively analyzed by HPLC using the conditions in Table 2.

TABLE 2

| Conditions for quantitative analysis of paclitaxel | |
|---|---|
| Instrument | HPLC (Waters, U.S.A.) |
| Column | Capcell Pack C18 UG120 (length: 250 mm, inner diameter: 4.6 mm) |
| Column temperature | 40° C. |
| Mobile phase | acetonitrile:water (20%–100% gradient) |
| Fluid speed | 1.0 ml/min |
| Injection volume | 10 $\mu$l |
| Detector | UV (227 nm), ATTE = 3 |

TABLE 3

Effect of the temperature changes on the growth of the Taxus genus plant cells and the production level of paclitaxel.

| | Dried cell mass (g/L) | | Paclitaxel (mg/L) | |
|---|---|---|---|---|
| | Day 21 | Day 42 | Day 21 | Day 42 |
| *T. baccata* | | | | |
| Culture at 24° C. | 7.8 | 10.1 | 0.3 | 0.6 |
| 24° C.->29° C. | 7.3 | 10.4 | 0.3 | 0.7 |

TABLE 3-continued

Effect of the temperature changes on the growth of the
Taxus genus plant cells and the production level of paclitaxel.

|  | Dried cell mass (g/L) | | Paclitaxel (mg/L) | |
|---|---|---|---|---|
|  | Day 21 | Day 42 | Day 21 | Day 42 |
| *T. chinensis* Hu-1 | | | | |
| Culture at 24° C. | 7.5 | 11.1 | 0.9 | 1.7 |
| 24° C.->29° C. | 7.3 | 9.5 | 0.8 | 2.9 |
| *T. chinensis* SYG-1 | | | | |
| Culture at 24° C. | 14.3 | 18.1 | 25.1 | 46.7 |
| 24° C.->29° C. | 14.1 | 18.5 | 24.3 | 93.2 |
| *T. cuspidate* | | | | |
| Culture at 24° C. | 8.5 | 12.4 | 0.5 | 1.1 |
| 24° C.->29° C. | 8.1 | 11.9 | 0.8 | 2.3 |
| *T. x media* | | | | |
| Culture at 24° C. | 11.6 | 14.2 | 3.4 | 7.6 |
| 24° C.->29° C. | 10.9 | 14.7 | 3.2 | 13.2 |

EXAMPLE 2
Temperature Effect on the Plant Cell Growth

SYG-1 cell culture which had been cultivated previously for 15 days in B5 medium supplemented with 500 mg/ml of casein hydrolysate was inoculated to 75 ml of the medium in Table 1 hydrolysate in a 250 ml Erlenmeyer flask, and cultivated for 20 days at 20° C., 24° C., 29° C., 32° C., and 36° C. The dried cell weight (DCW) at the time of the inoculation was 12 g/L. The dried cell mass was measured by using the method in Example 1 to determine the optimum growth temperature. The results of the dried cell mass is shown in FIG. 1 (-●-:20° C.; -■-:24° C.; -▲-:29° C.; -▼-:32° C.; -♦-:36° C.).

As can be seen in FIG. 1, the dried cell mass for the plant cells grown at 20° C., 24° C., 29° C., 32° C. and 36° C. were 8.23, 12.3, 6, 4.5 and 3.8 g/L, respectively, at day 13.

EXAMPLE 3
Effect of the Temperature Change During the Plant Cell Culture on the Cell Growth and the Production Level of Paclitaxel.

To determine the temperature change at which the cells were continuously grown after the cells were grown sufficiently at 24° C., the plant cell, *Taxus chenensis* SYC-1 was grown continuously under the following conditions: (1) temperature of the medium was 24° C. during the culture (hereinafter, referred to as '24° C. control group' for convenience); (2) temperature of the medium was 24° C. up to day 21 and changed to 29° C. (24° C.–29° C. test group); (3) temperature of the medium was 24° C. up to day 21 and changed to 32° C. (24° C.–32° C. test group); (4) temperature of the medium was 24° C. up to day 21 and changed to 20° C. (24° C.–20° C. test group). The dried cell mass and the amount of produced paclitaxel were analyzed.

Figure 2:
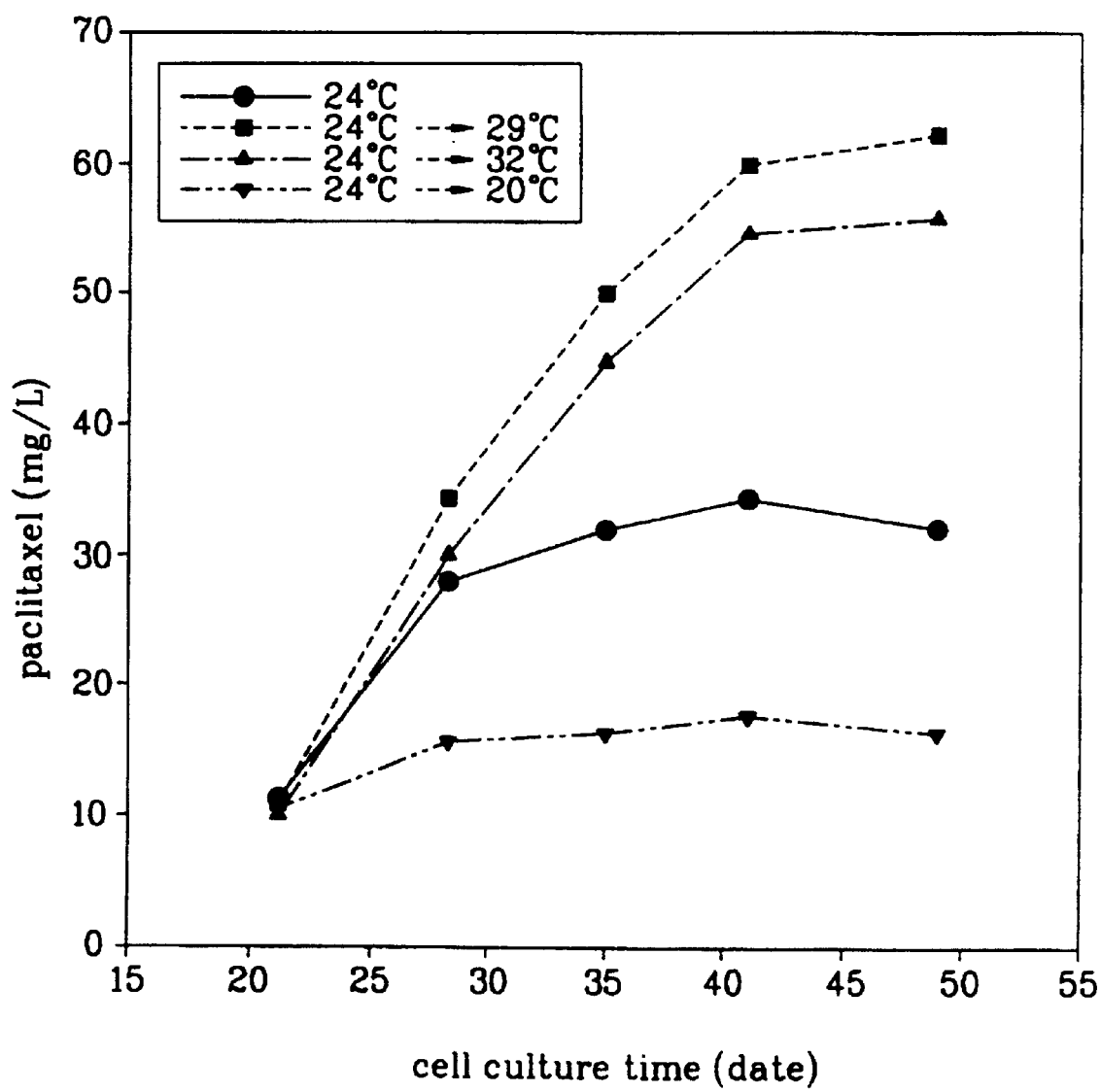
FIG. 2 is a graph showing the effect of the temperature change during the culture of *Taxus chinensis* SYG-1 on paclitaxel production.

SYG-1 cell culture which had been cultivated previously for 14 days in B5 medium supplemented with 500 mg/L of casein hydrolysate was inoculated to 75 ml of the medium in Table 1 hydrolysate in a 250 ml Erlenmeyer flask, and cultivated at 24° C. After 7 days, 10 g/L of maltose was added to each flask to continue the culture. At day 21, 20 g/L of maltose were added to all of the flasks. At day 21, among the 4 test groups, the cultivation temperature was maintained at 24° C. for one of the group. For the other groups, the temperature was changed to 29° C. (24° C.–29° C. test group); to 32° C. (24° C.–32° C. test group) and to 20° C. (24° C.–20° C. test group) respectively, and cultivated continuously. After finishing the cell culture, 7 ml of the culture from each group was sampled to determine the dried cell mass and the amount of paclitaxel produced according to the method described in Example 1. The results are shown in Table 4 and FIG. 2. (-●-:24° C. control group; -■-:24° C.–29° C. test group; -__-:24° C.–32° C. test group; -__-:24° C.–20° C. test group). The 24° C.–29° C. test group had the highest paclitaxel production level.

TABLE 4

Effect of the temperature change on growth

| Temperature change at | Dried cell mass (g/L) | |
|---|---|---|
| day 21 | day 21 | day 42 |
| 24° C. | 14.1 | 18.1 |
| from 24° C. to 29° C. | 14.2 | 19.2 |
| from 24° C. to 32° C. | 14.2 | 17.9 |
| from 24° C. to 20° C. | 14.5 | 15.8 |

EXAMPLE 4
Effect of the Time-point of the Temperature Change on the Growth and the Paclitaxel Production The cells were cultivated as described in Example 3 except that the time-point of the temperature change and the cultivation temperature were varied. The dried cell mass and the amount of paclitaxel produced were analyzed.

Figure 3:
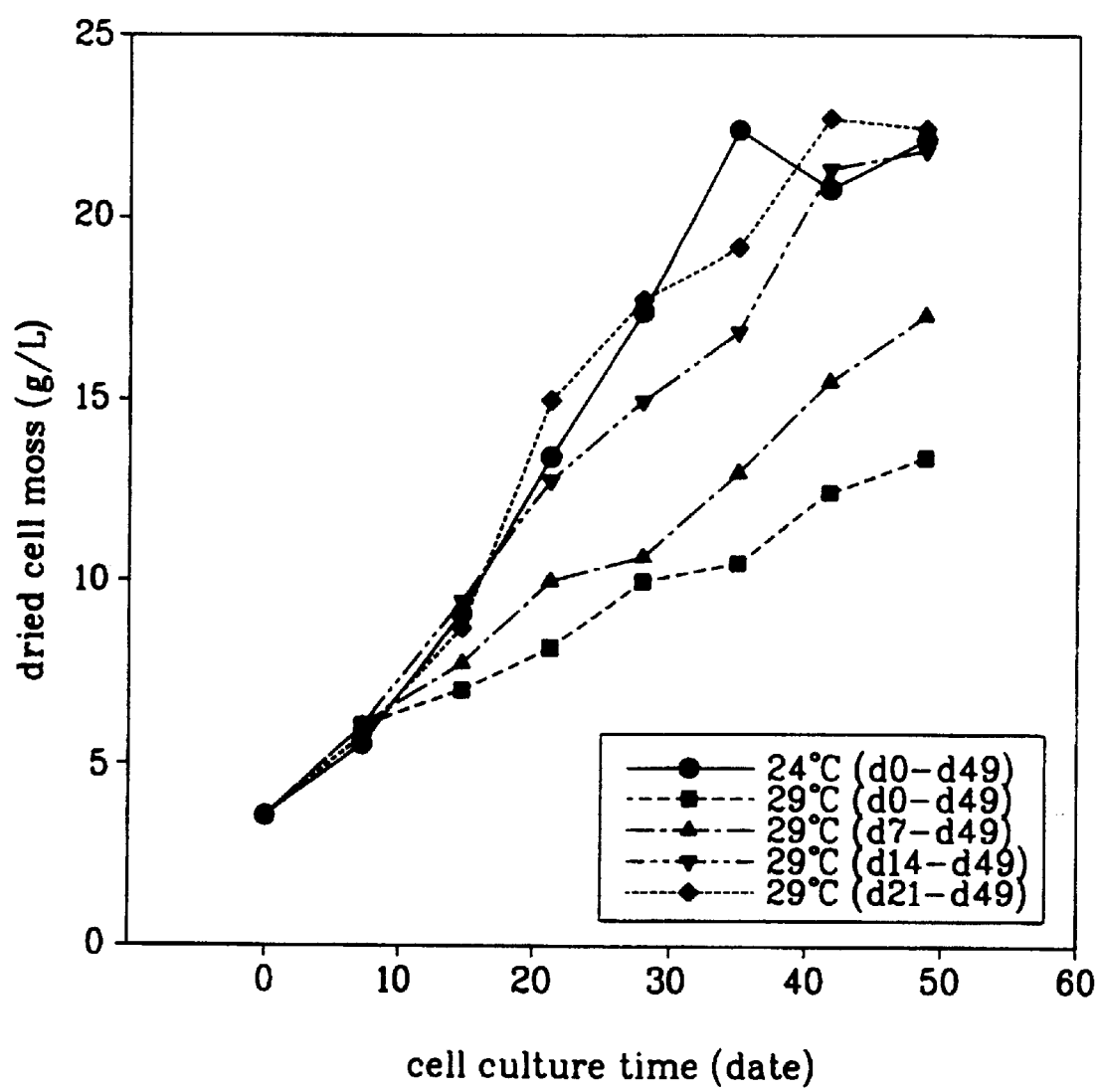
FIG. 3 is a graph showing the effect of the time-point of the temperature change on the growth of *Taxus chinensis* SYG-1.

The dried cell mass and the amount of produced paclitaxel were determined for the groups that were cultivated at 24° C. for 49 days, at 29° C. for 49 days, at 29° C. from day 8, at 29° C. from day 15 and at 29° C. from day 22 by using the method described in Example 1. The results are shown in FIG. 3 and In Table 5.

TABLE 5

Effect of the time-point of the temperature change on the amount of the produced paclitaxel.

| | Produced Paclitaxel (mg/L) | |
|---|---|---|
| Time-point of temperature change | 21st day | 49th day |
| 24° C. for 49 days | 26.0 | 28.8 |
| 29° C. for 49 days | 17.8 | 76.5 |
| 24° C. for 7 days, 29° C. from 8th day | 32.2 | 74.9 |
| 24° C. for 14 days, 29° C. from 15th day | 45.8 | 110.3 |
| 24° C. for 21 days, 29° C. from 22nd day | 26.7 | 137.5 |

EXAMPLE 5
Effect of Inoculation at a High Concentration

Effect of inoculation at a high concentration and the temperature change during the culture on the growth and the paclitaxel production level were determined. In Test group 1, the SYG-1 cells were cultivated in B5 medium supplemented with 500 mg/L of casein hydrolysate for 14 days, inoculated in the medium in Table 1 at a 1:4 ratio and cultivated at 24° C. for 14 days and subsequently cultivated at 24° C. after adding 3% maltose. The dried cell weight (DCW) at the time of the inoculation was 11.5 g/L. In Test group 2, all of the conditions were identical as in Test group 1 except that the cultivation temperature was changed to 29° C. after the 14th day. In the Test group 3, the cells were concentrated twice for the inoculation and cultivated at 24° C. In Test group 4, all of the conditions were identical as in Test group 3 except that the cultivation temperature was changed to 29° C. after the 14th day. The dried cell mass and the amount of produced paclitaxel were determined for the 4 Test groups at day 14, at day 28 and at day 42. The results are shown in Tables 6 and 7.

TABLE 6

Dried cell mass of Test groups inoculated at high concentration (g/L).

| Test group Day | 1 | 2 | 3 | 4 |
|---|---|---|---|---|
| day 14 | 9.36 | 9.00 | 11.19 | 11.23 |
| day 28 | 15.12 | 14.68 | 15.94 | 17.49 |
| day 42 | 17.03 | 18.34 | 15.03 | 16.42 |

TABLE 7

Content of paclitaxel (mg/L) and production level per unit dried cell mass (mg/g) of Test groups inoculated at high concentration.

| Test group Day | 1 | 2 | 3 | 4 |
|---|---|---|---|---|
| day 14 | 1.54 mg/L | 1.30 mg/L | 8.7 mg/L | 8.0 mg/L |
|  | 0.16 mg/g | 0.14 mg/g | 0.78 mg/g | 3.01 mg/g |
| day 28 | 23.05 mg/L | 30.65 mg/L | 39.87 mg/L | 47.57 mg/L |
|  | 1.52 mg/g | 2.09 mg/g | 2.50 mg/g | 2.72 mg/g |
| day 42 | 32.90 mg/L | 48.35 mg/L | 35.87 mg/L | 51.83 mg/L |
|  | 1.93 mg/g | 2.65 mg/g | 2.39 mg/g | 3.16 mg/g |

EXAMPLE 6

Effect of High Concentration Inoculation and High Saccharide Concentration.

The effects of inoculating the cells at a high concentration along with the effect of the temperature change during the culture and of a high saccharide concentration were observed. In Test group 1, the SYG-1 cells were cultivated in B5 medium supplemented with 500 mg/L of casein hydrolysate for 14 days, inoculated in the medium in Table 1 at a 1:4 ratio and cultivated at 24° C. for 14 days and subsequently cultivated at 24° C. after adding 3% maltose. The dried cell weight (DCW) at the time of the inoculation was 12 g/L. In Test group 2, the medium contained 6% maltose initially, and the maltose was not replenished during the culture. In Test group 3, all the conditions were identical as in Test group 2 except that the cells were concentrated twice for the inoculation. In the Test group 4, all of the conditions were identical as in Test group 3 except that the cultivation temperature was changed to 29° C. after the 14th day. The dried cell mass and the amount of produced paclitaxel were determined for the 4 Test groups at day 14, day 28 and day 42. The results are shown in Tables 8 and 9.

TABLE 8

Dried cell mass when inoculated at high concentration (g/L).

| Test group Day | 1 | 2 | 3 | 4 |
|---|---|---|---|---|
| day 14 | 9.36 | 6.34 | 9.63 | 9.65 |
| day 28 | 15.12 | 15.88 | 12.75 | 14.22 |
| day 42 | 17.03 | 11.24 | 12.37 | 15.74 |

TABLE 9

Content of paclitaxel (mg/L) and production level per unit dried cell mass (mg/g) of the Test groups inoculated at a high concentration.

| Test group day | 1 | 2 | 3 | 4 |
|---|---|---|---|---|
| day 14 | 1.54 mg/L | 1.95 mg/L | 13.57 mg/L | 16.40 mg/L |
|  | 0.16 mg/g | 0.31 mg/g | 1.41 mg/g | 1.70 mg/g |
| day 28 | 23.05 mg/L | 48.80 mg/L | 48.13 mg/L | 79.40 mg/L |
|  | 1.52 mg/g | 3.07 mg/g | 3.77 mg/g | 5.58 mg/g |
| day 42 | 32.90 mg/L | 42.20 mg/L | 33.20 mg/L | 78.23 mg/L |
|  | 1.93 mg/g | 3.75 mg/g | 2.68 mg/g | 4.97 mg/g |

As clearly illustrated and demonstrated as above the present invention provides an efficient method for mass production with a high yield of paclitaxel that can be applied industrially.

What is claimed is:

1. A method for mass production of paclitaxel comprising the steps of:
   (i) cultivating Taxus plant cells in a culture comprising a liquid medium suitable for growth of said cells at a cultivation temperature of 20° C. to 25° C. until exponential growth phase has been reached; then
   (ii) increasing the cultivation temperature to between 26° C. and 32° C.;
   (iii) maintaining the cultivation at the increased cultivation temperature for between one and forty-two days; and
   (iv) recovering paclitaxel from said culture.

2. The method for mass production of paclitaxel according to claim 1, wherein the cultivation temperature is increased at or later than day 10 after the initiation of the cultivation.

3. The method for mass production of paclitaxel according to claim 1, wherein the culture is supplemented with 10 g/L to 100 g/L of carbon source one or more times between 5 days and 30 days after the initiation of the cultivation.

4. The method for mass production of paclitaxel according to claim 1, wherein the inoculation concentration of Taxus cells in step (i) is greater than or equal to 4 grams dry mass of cells per liter of medium.

5. The method for mass production of paclitaxel according to claim 4, wherein said liquid medium initially comprises saccharide at a concentration higher than 40 g/L.

6. The method of claim 1, which further comprises isolating the cells after growth at a cultivation temperature of between 26° C. and 32° C., by removal of said cells from growth medium.

7. The method for mass production of paclitaxel according to claim 1, wherein the cultivation temperature in step (i) is between 20° C. and 25° C. and the cultivation temperature in step (ii) is between 27° C. and 32° C.

* * * * *